(12) United States Patent
Hwang et al.

(10) Patent No.: US 7,037,939 B2
(45) Date of Patent: May 2, 2006

(54) COMPOUND AND DERIVATIVE OF GABAPENTIN

(75) Inventors: Jenn-Tsang Hwang, Hsinchu (TW); Yu-Long Chang, Hsinchu (TW); Chung-Niang Yao, Hsinchu (TW); Chrong-Shiong Hwang, Hsinchu (TW)

(73) Assignee: Industrial Technology Research Institue, Hsinchu (TW)

( * ) Notice: Subject to any disclaimer, the term of this patent is extended or adjusted under 35 U.S.C. 154(b) by 150 days.

(21) Appl. No.: 10/748,191

(22) Filed: Dec. 31, 2003

(65) Prior Publication Data
US 2004/0248811 A1    Dec. 9, 2004

(30) Foreign Application Priority Data
Dec. 31, 2002    (TW) ............................... 91138154 A

(51) Int. Cl.
*A61K 31/24*    (2006.01)
*C07C 235/41*    (2006.01)
(52) U.S. Cl. ........................... 514/534; 560/41
(58) Field of Classification Search ............ 514/18
See application file for complete search history.

(56) References Cited

U.S. PATENT DOCUMENTS
2003/0216469 A1* 11/2003 Bryans et al. .............. 514/534

* cited by examiner

*Primary Examiner*—Bruce R. Campell
*Assistant Examiner*—Thomas S. Heard
(74) *Attorney, Agent, or Firm*—Bacon & Thomas, PLLC

(57) ABSTRACT

The present invention relates to a compound represented as formula (I):

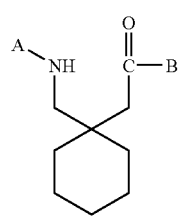

wherein
A is R2-N(R3R4),

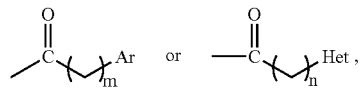

wherein Ar is a substituted or unsubstituted phenyl group, m is an integer between 0 to 4, Het is a substituted or unsubstituted 4 to 8 member heterocyclic group, n is an integer between 0 to 4; $R_3$ and $R_4$ are independently H,

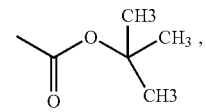

or

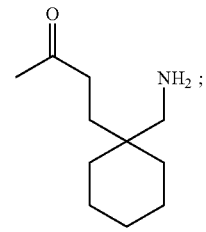

$R_2$ is

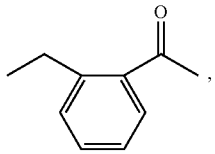

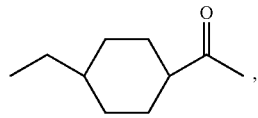

or
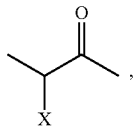
wherein X is $(CH_2)_y$—Ar', $R_6$, or $(CH_2)_z$-Het', wherein Ar' is a substituted or unsubstituted phenyl group, y is an integer between 0 to 2, $R_6$ is a substituted or unsubstituted linear or a branched $C_{1-10}$ alkyl group, z is an integer between 0 to 2, and Het' is a 6 to 12 member heterocyclic group;
B is $OR_1$ or
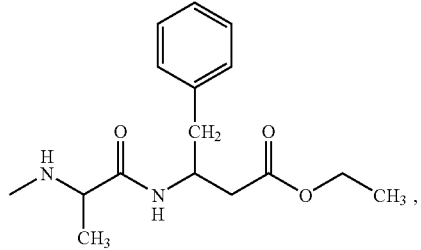
wherein $R_1$ is H or $C_{2-5}$ alkyl group.
2 Claims, No Drawings

COMPOUND AND DERIVATIVE OF GABAPENTIN

BACKGROUND OF THE INVENTION

1. Field of the Invention

The present invention relates to a compound or derivatives of gabapentin, especially a compound or derivatives of gabapentin for medical purposes.

2. Description of Related Art

Gabapentin is used widely in the treatment of epilepsy and in pain syndrome therapy and in 2001; its global sales reached US$1.47 billion. However, the drug has poor oral bioavailability, and 900 to 4800 mg in dosage for three times per day is required to approach the desired efficacy. However, it was found that the greater dosage in administration did not result in relative adsorption enhancement. Moreover, the change of the administration method did not increase the oral bioavailability. Therefore, according to the prodrug concepts, if the gabapentin can be designed as a highly bioavailable prodrug to reduce the dosage amount and regime such that it need be taken only one time per day, then the convenience for the patients will be largely promoted.

Previously, the cyclic amino acid (gabaperitin) was used to conjugate with the twenty natural amino acids to produce its derivatives and increase its standing time in the body. The related art is achieved by chemical synthesis, which describes the synthesis pathway, yet the related tests were not extended to prove the efficacy of the designed derivative.

SUMMARY OF THE INVENTION

The object of the present invention is to provide a compound derived from gabapentin, which can be used as a prodrug of gabapentin to increase its bioavailability in vivo.

To achieve the object, the present gabapentin derivative is a compound of a formula (I):

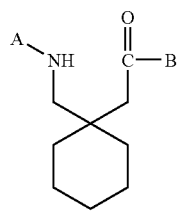

(I)

wherein
A is R2-N(R3R4),

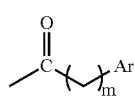

or

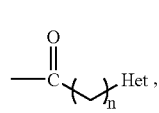

wherein Ar is a substituted or unsubstituted phenyl group, m is an integer between 0 to 4, Het is a substituted or unsubstituted 4 to 8 member heterocyclic group, n is an integer between 0 to 4; $R_3$ and $R_4$ are independently H,

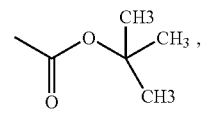

or

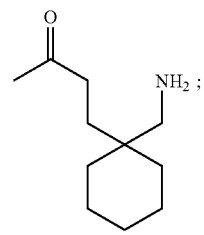

$R_2$ is

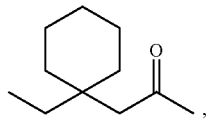

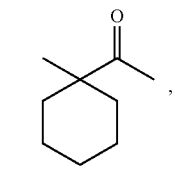

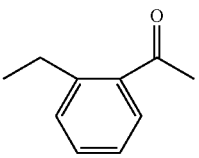

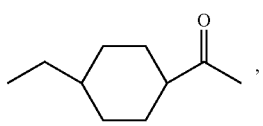

or

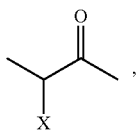

wherein X is $(CH_2)_y$—Ar', $R_6$, or $(CH_2)_n$-Het', wherein Ar' is a substituted or unsubstituted phenyl group, y is an integer between 0 to 2, $R_6$ is a substituted or unsubstituted linear or branched $C_{1-10}$ alkyl group, z is an integer between 0 to 2, and Het' is a 6 to 12 member heterocyclic group;

B is $OR_1$ or

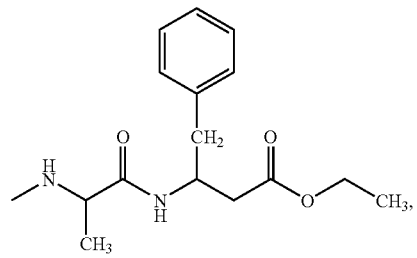

wherein $R_1$ is H or $C_{2-5}$ alkyl group.

In the present invention, one or several specific unnatural amino acids are conjugated with a gabapentin moeity to produce new compounds whose hydrophorbility is better than that of the original gabapentin. The new compounds are tested in the Caco-2 cell model, and the best transmission rate of the examples is ten fold more than the parent. Therefore, the compound with gabapentin moiety of the present invention increases the oral bioavailability in human patients. Moreover, the new structure of the compounds with gabapentin moiety of the present invention is a specific achievement of the novel concept in drug design.

In the present compound, A is $R_2$—$N(R_3R_4)$,

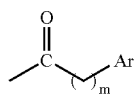

or

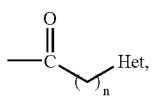

wherein Ar is a substituted or unsubstituted phenyl group, preferably

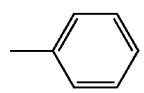

or

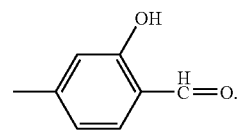

In the present compound, Het is a substituted or unsubstituted 4 to 8 member heterocyclic group, preferably

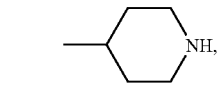

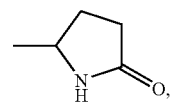

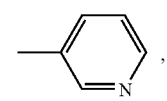

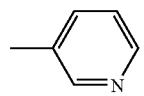

or

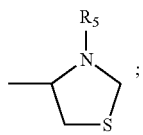

and $R_5$ is H or

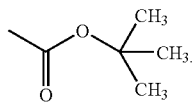

In the present compound, X preferably is $(CH_2)_y$—Ar', $R_6$, or $(CH_2)_n$-Het', wherein Ar' is a substituted or unsubstituted phenyl group, preferably

or

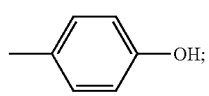

and $R_6$ is a substituted or unsubstituted linear or branched $C_{1-10}$ alkyl group, preferably

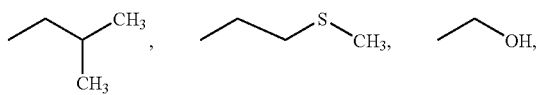

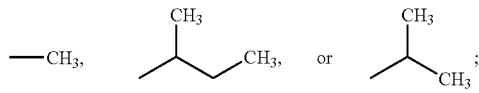

Het' is a 6 to 12 member heterocyclic group, preferably

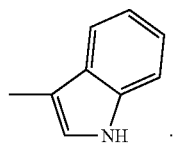

DETAILED DESCRIPTION OF THE PREFERRED EMBODIMENT

For the greater understanding of the present art by those skilled in the art, there are thirty-eight preferred embodiments specifically described as follows.

In the present invention, the preparing method of each embodiment is represented by the synthesis pathways in Scheme 1.

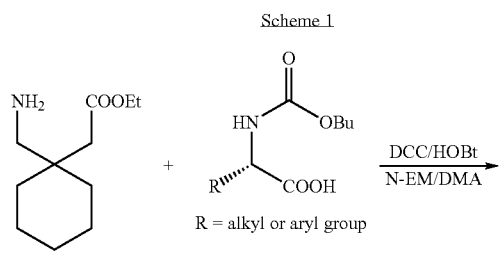

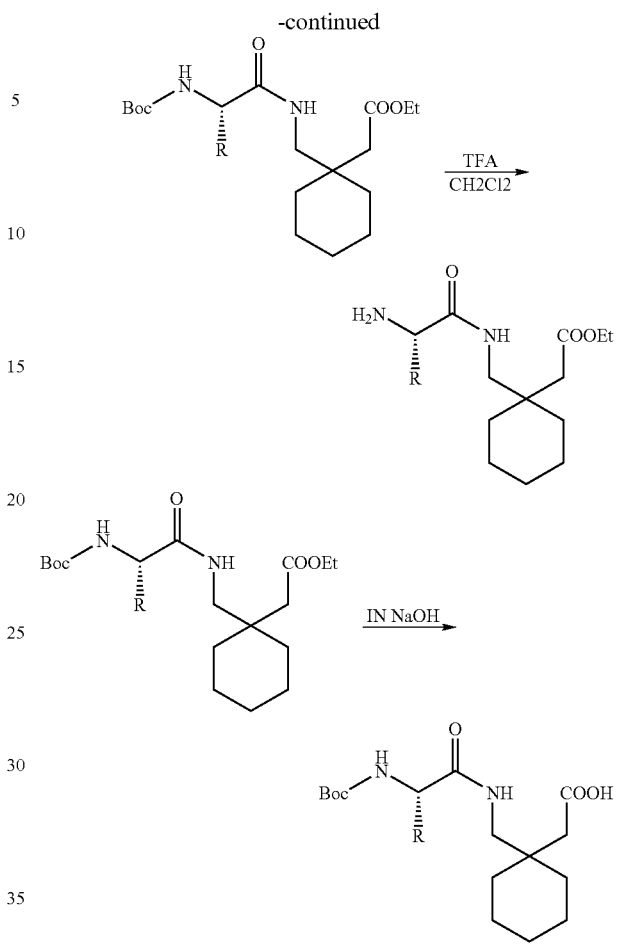

The establishment of the intestinal absorption model in vitro is processed by an activity selection in vitro and showed as follows:

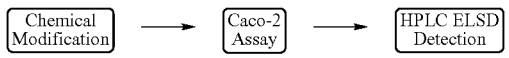

The activity selection in vitro is used to select the gabapentin derivative.

The common use of the activity selection model for the in vitro intestinal absorption comprises: (1) Carcinoms (Caco-2); (2) Using Chamber; (3) Everted Gut Sac. Basically, there is no difference for those three drug-activity-selection models when they are used for evaluating the activity selection. However, in terms of the cell source from human, a cell line is predominant. Moreover, with the cellular metabolism being similar to human intestines, Caco-2 becomes an excellent tool in the study of intestine absorption. Therefore, in the comparison of the in vitro transmission rate between gabapentin and gabapentin derivatives, the Caco-2 system is still the favorable model.

The research for studying gabapentin and the derivatives thereof in the present invention includes: Caco-2 cell activation, Caco-2 monolayer cell cultivation, resistance value measurement, effect of time to gabapentin transmission rate, and comparison of transmission rate between gabapentin and gabapentin derivatives. In constructing the Caco-2 monolayer, the original cell line is the human colon adenocarcinoma cell (Caco-2), and its data sheet is listed as Table 2.

The Caco-2 cell is activated appropriately, and seeded in the transwell at 37° C. in an amount of about 1×10$^5$. The aliquot is cultivated in 5% $CO_2$ at 37° C. and replaced with a fresh medium every 3 to 4 days, and then the monolayer cell is obtained by the 21 days cultivation. The integrity of the Caco-2 cell is further characterized by tissue section and resistance value measurement.

Embodiment 1

Preparation of the NBoc-D-Leu.GBP.OH

In the present embodiment, the chemicals and solvents are commercially available from Aldrich®, Lancaster®, or TEDIA® chemical degree products and never purified before usage; the (1-Aminomethyl-cyclohexyl)-acetic acid ethyl ester (GBPOEt) is synthesized according to the conventional methods. The IUPAC chemical nomenclature of the NBoc-D-Leu.GBP.OH is {1-[(2R-tert-Butoxycarbonylamino-4-methyl-pentanoylamino)-methyl]-cyclohexyl}-acetic acid.

0.8 g (3.4 mmol) of 2R-tert-Butoxycarbonylamino-4-methyl-pentanoic acid (BocN-D-LeuOH) is mixed with 0.8 g (3.41 mmol) of (1-Aminomethyl-cyclohexyl)-acetic acid ethyl ester (GBPOEt) and then dissolved in THF (6 mL) and DMA (2 mL). Then 460 μl (3.74 mmol) of N-ethylmorpholine (N-EM) and 0.52 g (3.74 mmol) of 1-hydroxybenzotriazole hydrate (HOBT) are further added. After dissolving completely, the solvent is cooled to 0° C., then 0.76 g (3.74 mmol) of 1,3-dicyclohexylcarbodiimide (DCC) is added and stirred for 1 hr. After the temperature is returned to 25 to 27° C., the mixture is stirred for another 10 to 15 hr. Then, the solid portion is filtrated, and the filtrate is diluted with 25 ml of ethyl acetate, and further washed individually and orderly with 10 ml of saturated $NaHCO_3$, 10% of citric acid, and saturated $NaHCO_3$. The organic layer is dried, filtrated, and concentrated to remove the solvent fraction and obtain the crude product. The crude product is further chromatographically filtrated by alumina oxide with the elute solvent of ethyl acetate/hexane 2:1 to obtain 0.69 g of a viscous liquid product (yield: 49.3%).

$^1$H NMR (200 MHz, $CDCl_3$): δ 0.94 (d, J=5.29 Hz, 6H), 1.30 (t, J=7.12 Hz, 3H), 1.21–1.72 (m, 15H, cyclohexyl, Leucine-CH2CH2CH—), 1.43 (9H, t-butyl), 2.29 (s, 2H), 3.25–3.31 (m, 2H), 4.06–4.20 (m, 4H), 4.96 (br d, J=7.80 Hz, 2H), 6.85 (br s, 2H).

Further, 0.69 g of {1-[(2-tert-Butoxycarbonylamino-4-methyl-pentanoylamino)-methyl]-cyclohexyl}-acetic acid ethyl ester and 10 ml of MeOH are added in the 50-ml bottle, then 2.5 ml of 2N NaOH is added and heated to 60° C. for 1 hr. After cooling, the mixture is neutralized to around pH 7.0 by 3N HCl and then vacuum concentrated to a nearly viscous state. Then, 10 ml of $H_2O$ is added and adjusted to pH ~1.0 by 3N HCl and extracted twice with 10 ml of ethyl acetate. The organic layer is further washed with 10 ml of saturated salt solution, dried with magnesium sulfate anhydrate, filtrated and concentrated to obtain 0.52 g of product (yield: 80.8%).

$^1$H NMR (200 MHz, $CDCl_3$): δ 0.94 (d, J=5.26 Hz, 6H), 1.32–1.92 (m, 15H, cyclohexyl, Leucine-CH2CH2CH—), 1.44 (9H, t-butyl), 2.17 (s, 2H), 3.30 (s, 2H), 4.96 (br m, 1H), 7.29–7.34 (br m, 2H).

Embodiment 2

Preparation of the $NH_2$ GBP-GBPOEt

The IUPAC chemical nomenclature of the $NH_2$ GBP-GBPOEt is (1-{[2-(1-Aminomethyl-cyclohexyl)-acetylamino]-methyl}-cyclohexyl)-acetic acid ethyl ester.

1.6 g (5.9 mmol) of [1-(tert-Butoxy-carbonylamino-methyl)-cyclohexyl]-acetic acid (BocN-GBPOH) is mixed with 1.39 g (5.9 mmol) of (1-Aminomethyl-cyclohexyl)-acetic acid ethyl ester (GBPOEt) and then dissolved in THF (8 mL) and DMA (4 mL). Then 820 μl (6.49 mmol) of N-ethylmorpholine (N-EM) and 0.8 g (6.49 mmol) of 1-hydroxybenzotriazole hydrate (HOBT) are further added. After dissolving completely, the solvent is cooled to 0–5° C.; then 1.33 g (6.49 mmol) of 1,3-dicyclohexylcarbodiimide (DCC) is added and stirred for 1 hr. After the temperature is returned to 25 to 27° C., the mixture is stirred for another 18 hr. Then, the solid portion is filtrated, and the filtrate is diluted with 25 ml ethyl acetate, and further washed individually and orderly with 15 ml of saturated $NaHCO_3$, 10% of citric acid, and saturated $NaHCO_3$. The organic layer is dried, filtrated, and concentrated to remove the solvent fraction and obtain the crude product. The crude product is further chromatographically filtrated by alkali aluminum oxide with the elute consisting of ethyl acetate/hexane (1:3) to obtain 2.06 g of a white viscous liquid product [1-({2-[1-(tert-Butoxy-carbonylamino-methyl)-cyclohexyl]-acetylamino}-methyl)-cyclohexyl]-acetic acid ethyl ester.

$^1$H NMR (200 MHz, $CDCl_3$): δ 1.26 (t, J=7.10 Hz, 3H), 1.25–1.82 (m, 20H, cyclohexyl), 1.43 (9H, t-butyl), 2.15 (s, 2H), 2.32 (s, 2H), 3.13 (d, J=6.80 Hz, 2H), 3.30 (d, J=6.20 Hz, 2H) 4.08–4.20 (m, 2H), 5.46–5.52 (br m, 1H), 7.02 (br s, 1H).

Further, 2.06 g of [1-({2-[1-(tert-Butoxycarbonylamino-methyl)-cyclohexyl]-acetylamino}-methyl)-cyclohexyl]-acetic acid ethyl ester (the productivity of 77.1%) and 13 ml of $CH_2Cl_2$ are added in the 50-ml bottle. Then, 2.5 ml of trifluoroacetatic acid is added under 25° C., and stirred at 25 to 28° C. for 3 hr. The mixture is further vacuum concentrated to a nearly viscous state and diluted with 20 ml ethyl acetate. Then, the mixture is extracted twice with 10 ml of saturated $NaHCO_3$. The organic layer is further washed with 10 ml of a saturated salt solution, dried with magnesium sulfate anhydrate, filtrated and concentrated to obtain 1.6 g of a final product (yield: 99%).

$^1$H NMR (200 MHz, $CDCl_3$): δ 1.26 (t, J=7.10 Hz, 3H), 1.25–1.72 (m, 20H, cyclohexyl x2), 2.32 (s, 2H), 2.45 (s, 2H), 2.97 (s, 2H), 3.26 (d, J=6.00 Hz, 2H), 4.14-(q, J=7.10 Hz, 2H), 6.8 (br s, 1H), 7.21–7.28 (m, 1H)

Embodiments 3 to 38

Embodiments 3 to 38 are similar methods wherein the products are prepared as Table 1.

The results of the cell transmission rate in the products of 5 embodiments 3 to 38 are further listed in Table 1.

TABLE 1

The results of products and cell transmission rate in the embodiments

| No. of Embodiment | Sample Name and IUPAC Nomenclature | MW. | Analysis Method | Caco-2 Cell Mean Total Transmission rate 4 h (%) | gbp-prodrug/gbp Transmission Fold |
|---|---|---|---|---|---|
| Control 1 | GBP.HCl | 171 + 36.45 | ELSD | 1.1 | 1 |
| Embodiment 1 | NBoc-D-Leu.GBP.OH {1-[(2-tert-Butoxycarbonyl-amino-4-methyl-pentanoylamino)-methyl]-cyclohexyl}-acetic acid | 384 | ELSD | 29 | 26.4 |
| Embodiment 2 | NH$_2$GBP-GBPOEt(1-{[2-(1-Aminomethyl-cyclohexyl)-acetylamino]-methyl}-cyclohexyl)-acetic acid ethyl ester | 352 | ELSD | 10.25 | 9.3 |
| Embodiment 3 | NBoc-D-PhG.GBP.OH {1-[(2-tert-Butoxycarbonyl-amino-2-phenyl-acetylamino)-methyl]-cyclohexyl}-acetic acid | 404 | ELSD | 3.1 | 2.8 |
| Embodiment 4 | NBoc-D-Phe.GBP.OH {1-[(2-tert-Butoxycarbonyl-amino-3-phenyl-propionylamino)-methyl]-cyclohexyl}-acetic acid | 418 | ELSD | 10 | 9.1 |
| Embodiment 5 | NBoc-D-Met.GBP.OH {1-[(2-tert-Butoxycarbonyl-amino-4-methylsulfanyl-butyryl-amino)-methyl]-cyclohexyl}-acetic acid | 402 | ELSD | 26 | 23.6 |
| Embodiment 6 | NBoc.GBP.GBP.OH [1-({2-[1-(tert-Butoxycarbonyl-amino-methyl)-cyclohexyl]-acetylamino}-methyl)-cyclo-hexyl]-acetic acid | 424 | ELSD | 27 | 24.5 |
| Embodiment 7 | NH2.INP.GBP.OEt (1-{[(Piperidine-4-carbonyl)-amino]-methyl}-cyclohexyl)-acetic acid ethyl ester | 310 | ELSD | 1 | 0.9 |
| Embodiment 8 | Tol-NHGBP.OEt [1-(Benzoylamino-methyl)-cyclohexyl]-acetic acid ethyl ester | 317 | ELSD | 21.4 | 19.5 |
| Embodiment 9 | NH2-ACHC.GBP.OEt (1-{[(1-Amino-cyclohexane-carbonyl)-amino]-methyl}-cyclohexyl)-acetic acid ethyl ester | 324 | ELSD | 10.4 | 9.5 |
| Embodiment 10 | NBocD-Ser-GBPOH {1-[(2-tert-Butoxycarbonyl-amino-3-hydroxy-propionyl-amino)-methyl]-cyclohexyl}-acetic acid | 358 | ELSD | 20.7 | 18.8 |
| Embodiment 11 | NH2.D-Ala-GBPOEt {1-[(2-Amino-propionylamino)-methyl]-cyclohexyl}-acetic acid ethyl ester | 270 | ELSD | 17.6 | 16.0 |
| Embodiment 12 | NH2.GBP-D-Ala-L-PheOEt 2-{2-[2-(1-Aminoethyl-cyclo-hexyl)-acetylamino]-propionyl-amino}-3-phenyl-propionic acid ethyl ester | 417 | ELSD | 2.83 | 2.6 |
| Embodiment 13 | NH$_2$D-Leu-GBPOEt {1-[(2-Amino-4-methyl-pentanoyl- | 312 | ELSD | 12.37 | 11.2 |

TABLE 1-continued

The results of products and cell transmission rate in the embodiments

| No. of Embodiment | Sample Name and IUPAC Nomenclature | MW. | Analysis Method | Caco-2 Cell Mean Total Transmission rate 4 h (%) | gbp-prodrug/ gbp Transmission Fold |
|---|---|---|---|---|---|
| Embodiment 14 | NH₂D-Ser-GBPOEt {1-[(2-Amino-3-hydroxy-propionylamino)-methyl]-cyclo-hexyl}-acetic acid ethyl ester | 292 | ELSD | 10.95 | 10.0 |
| Embodiment 15 | NBocD-Phe-GBPOH {1-[(2-tert-Butoxycarbonyl-amino-3-phenyl-propionylamino)-methyl]-cyclohexyl}-acetic acid | 418 | ELSD | 0.93 | 0.8 |
| Embodiment 16 | NH₂D-Phe-GBPOEt {1-[(2-Amino-3-phenyl-propionyl-amino)-methyl]-cyclohexyl}-acetic acid ethyl ester | 346 | ELSD | 10.30 | 9.4 |
| Embodiment 17 | NH₂L-Ile-GBPOEt {1-[(2-Amino-3-methyl-pentanoyl-amino)-methyl]-cyclo-hexyl}-acetic acid ethyl ester | 312 | ELSD | 9.47 | 8.6 |
| Embodiment 18 | NH₂-2-MePhe-GBPOEt {1-[(2-Aminomethyl-benzoyl-amino)-methyl]-cyclohexyl}-acetic acid ethyl ester | 360 | ELSD | 2.13 | 1.9 |
| Embodiment 19 | NH₂—CH2-4-Cyhexl-GBPOEt (1-{[(4-Aminomethyl-cyclo-hexanecarbonyl)-amino]-methyl}-cyclohexyl)-acetic acid ethyl ester | 338 | ELSD | 11.14 | 10.1 |
| Embodiment 20 | NH₂GBP.D-Leu-GBPOEt [1-({2-[2-(1-Aminomethyl-cyclohexyl)-acetylamino]-4-methyl-pentanoylamino}-methyl)-cyclohexyl]-acetic acid ethyl ester | 465 | ELSD | 12.22 | 11.1 |
| Embodiment 21 | NH₂GBP.D-Phg-GBPOEt [1-({2-[2-(1-Aminomethyl-cyclohexyl)-acetylamino]-2-phenyl-acetylamino}-methyl)-cyclohexyl]-acetic acid ethyl ester | 485 | ELSD | 8.58 | 7.8 |
| Embodiment 22 | NH₂GBP.D-Phe-GBPOEt [1-({2-[2-(1-Aminomethyl-cyclohexyl)-acetylamino]-3-phenyl-propionylamino}-methyl)-cyclohexyl]-acetic acid ethyl ester | 499 | ELSD | 9.26 | 8.4 |
| Embodiment 23 | NH₂GBP.L-Pro-GBPOEt {1-[({1-[2-(1-Aminomethyl-cyclohexyl)-acetyl]-pyrrolidine-2-carbonyl}-amino)-methyl]-cyclohexyl}-acetic acid | 449 | ELSD | 10.73 | 9.8 |
| Embodiment 24 | (3-OMe4OH)Ph-GBPOEt{1-[(4-Hydroxy-3-methoxy-benzoyl-amino)-methyl]-cyclohexyl}-acetic acid ethyl ester | 349 | ELSD | 13.59 | 12.4 |
| Embodiment 25 | Pydone-GBPOEt(1-{[(5-Oxo-pyrrolidine-2-carbonyl)-amino]-methyl}-cyclohexyl)-acetic acid ethyl ester | 310 | ELSD | 5.68 | 5.2 |
| Embodiment 26 | NH₂D-Met-GBPOEt{1-[(2-Amino-4-methylsulfanyl-butyryl-amino)-methyl]-cyclohexyl}-acetic acid ethyl ester | 330 | ELSD | 9.02 | 8.2 |
| Embodiment 27 | 3pyridine-GBPOEt(1-{[(Pyridine-3-carbonyl)-amino]-methyl}-cyclohexyl)-acetic acid ethyl ester | 304 | ELSD | 9.39 | 8.5 |

TABLE 1-continued

The results of products and cell transmission rate in the embodiments

| No. of Embodiment | Sample Name and IUPAC Nomenclature | MW. | Analysis Method | Caco-2 Cell Mean Total Transmission rate 4 h (%) | gbp-prodrug/gbp Transmission Fold |
|---|---|---|---|---|---|
| Embodiment 28 | NH$_2$D-Ala-GBPOEt{1-[(2-Amino-propionylamino)-methyl]-cyclohexyl}-acetic acid ethyl ester | 270 | ELSD | 8.11 | 7.4 |
| Embodiment 29 | NH$_2$D-Val-GBPOEt{1-[(2-Amino-3-methyl-butyrylamino)-methyl]-cyclohexyl}-acetic acid ethyl ester | 298 | ELSD | 8.73 | 7.9 |
| Embodiment 30 | NH$_2$L-Phg-GBPOEt{1-[(2-Amino-2-phenyl-acetylamino)-methyl]-cyclohexyl}-acetic acid ethyl ester | 332 | ELSD | 11.87 | 10.8 |
| Embodiment 31 | NH$_2$D-hPhe-GBPOEt{1-[(2-Amino-4-phenyl-butyrylamino)-methyl]-cyclohexyl}-acetic acid ethyl ester | 358 | ELSD | 12.30 | 11.2 |
| Embodiment 32 | NH$_2$L-hPhe-GBPOEt{1-[(2-Amino-4-phenyl-butyrylamino)-methyl]-cyclohexyl}-acetic acid ethyl ester | 358 | ELSD | 1.76 | 1.6 |
| Embodiment 33 | NH$_2$D-Try-GBPOEt (1-{[2-Amino-2-(1H-indol-2-yl)-acetylamino]-methyl}-cyclohexyl)-acetic acid ethyl ester | 385 | ELSD | 9.97 | 9.1 |
| Embodiment 34 | NH$_2$L-Thz-GBPOEt(1-{[(Thiazolidine-4-carbonyl)-amino]-methyl}-cyclohexyl)-acetic acid ethyl ester | 314 | ELSD | 4.50 | 4.1 |
| Embodiment 35 | NH$_2$L-Tyr-GBPOEt (1-{[2-Amino-2-(4-hydroxy-phenyl)-acetylamino]-methyl}-cyclohexyl)-acetic acid ethyl ester | 362 | ELSD | 10.33 | 9.4 |
| Embodiment 36 | (3-Py)CH2CH2GBPOEt [1-({3-[(Pyridine-3-carbonyl)-amino]-propionylamino}-methyl)-cyclohexyl]-acetic acid ethyl ester | 375 | ELSD | 9.00 | 8.2 |
| Embodiment 37 | NBocL-Thz-GBPOEt 4-[(1-Ethoxycarbonylmethyl-cyclohexylmethyl)-carbamoyl]-thiazolidine-3-carboxylic acid tert-butyl ester | 414 | ELSD | 6.13 | 5.6 |
| Embodiment 38 | NBocL-Tyr-GBPOEt (1-{[2-tert-Butoxycarbonyl-amino-2-(4-hydroxy-phenyl)-acetylamino]-methyl}-cyclohexyl)-acetic acid ethyl ester | 462 | ELSD | 5.05 | 4.6 |

HPLC Analysis: Intersil ODS-3V 250*4.6 mm column, Solvent: MeOH/H$_2$O=10:90 to 70:30 with 0.1% of NH4OAc, Flow rate=1.0 ml/min, ELSD: Evaporative Light Scattering Detector. Every derivative has been repeated for 3 times in analysis, 4 hr later, the sample is analyzed for the transmission rate and then averaged to account its transmission fold.

TABLE 2

Human Colon Adenocarcinoma Cell Line Strain Data Sheet

| | |
|---|---|
| Strain Code No. | CCRC60018 |
| Cell Line | Caco-2 |
| Cell Strain Source | ATCC HTB-37 |
| Tissue Source | Colon, adenocarcinoma, human |
| Frozen Tube Volume | 1 ml    Concentration    1.3 × 10$^6$ |
| Frozen Date | 12.31.1999    Subculture No.    P23 |
| Survival Rate | 82.5% |
| Medium | 80% MEM (Eagle) with non-essential amino acids and Earle's BSS + 20% FBS |
| Cultivation Condition | 37° C., 5% CO$_2$ |
| Frozen Medium | 90% culture medium + 10% DMSO |
| Medium Replacement | 2 to 3 times per week |

TABLE 2-continued

Human Colon Adenocarcinoma Cell Line Strain Data Sheet

Subculture Dilution Ratio 1:2 to 1:3
Contamination Test  Negative for bacteria, fungi and mycoplasma Furthermore, for increasing the efficiency of drug-absorption through oral administration, these drugs are designed to pass the epithelium cells in small intestines by passive diffusion can enter the "body circulation". For facilitating the passive diffusion of drugs through the epithelium cells in small intestines, several biochemical features of the drugs are adjusted. These biochemical features of the suitable drugs comprise low molecular weight (such as <500 Da), water solubility, and proper hydrophilicity/hydrophobicity ratio (1.5<log P<4.0, with reference: Navia, chaturvedi, P. R. *Drug Discovery Today*, 1996, 1, 179–189). On the other hand, because gabapentin is a compound with high polarity and high hyrophilicity (log P=−1.1), gabapentin or its derivative is hard to pass the lipid layer of the small intestines epithelium cells. Therefore, compounds modified from the structure of gabapentin or its derivatives (as listed in Table 1) for functioning as prodrugs facilitate the passive diffusion through the epithelium cells in small intestines for entering blood circulation.

Embodiment 39

Oral Drug Absorption Test

Rats (3 male, Winstar rats) are fed with 300 mg/kg dosage of compounds. Plural blood samples are collected at different times (0, 0.5, 1, 2, 3, 8, 12, 24 hrs). The blood samples are centrifuged, and the concentration of gabapentin in the serum are analyzed with LC/MS/MS (MRM method, limitation of instruments 0.005 μg/mL). The results are listed in Table 3.

TABLE 3

Gabapentin prodrug concentration in rat blood (passive diffusion passage)

| Compound | Tmax** (hr) | C max*** (mg/mL) | AUC**** (mg.hr/mL) |
|---|---|---|---|
| Embodiment 2 NH$_2$.GBP.GBPOEt | 1.0 | 34.4 | 198.56 |
| Embodiment 29 NH$_2$.D-ValGBPOEt | 3.5 | 0.46 | 2.66 |
| Gabapentin HCl* | 2.0 | 2.53 | 13.30 |

*Gabapentin HCl is synthesized by the inventor;
**Tmax: the timing of maximum concentration of Gabapentin;
***Cmax: the maximum concentration of Gabapentin in blood;
****AUC: the area sum under the Gabapentin concentration curve, the higher value means the better absorption by intestine, calculated by WinNonLin ®.

The AUC value of the compound from Embodiment 2 is 14.9 times higher than Gabapentin HCl. The fact means that compound prepared in embodiment 2 enters blood circulation easily.

After reducing the dosage, compounds of gabapentin prodrugs were selected for further pharmacodynamic analysis. The rats are fed with 50 mg/kg dosage of gabapentin equivalency individually. The results are listed in Table 4. The results showed gabapentin prodrugs could be absorbed in animal intestine and degraded by intestinal enzymes to release gabapentin.

TABLE 4

Gabapentin released by prodrug blood analysis results in Rat

| Compound | Tmax (hr) | Cmax (mg/mL) | AUC(μg.hr/mL) |
|---|---|---|---|
| Embodiment 2 NH$_2$.GBP.GBP.OEt | 2.0 | 1.00 | 4.27 |
| NH$_2$.Gly GBPOH | 1.0 | 22.0 | 81.40 |
| NH$_2$.L-Phe.GBPOH | 2.0 | 2.71 | 44.37 |
| Gabapentin HCl | 1.0 | 32.3 | 122.26 |

NH$_2$.Gly.GBPOH prodrug can release gabapentin in the animal blood with an AUC value of 81.4, which is 0.67 times higher than that of gabapentin. On the other hand, although the maximum concentration Cmax of prodrug is lower than that of gabapentin, which also means lower side effect while still having effective concentration.

The experiments illustrated above in Embodiment 39 prove that the gabapentin derivatives in a prodrug form can ease the absorption of gabapentin derivatives by intestinal diffusion, and the gabapentin prodrugs in the blood promise the releasing of gabapentin. The prodrug idea can be further applied to other drugs.

From the above embodiments, it is found that the present gabapentin derivatives certainly enhance the cell transmission rate and promote the bioavailability of the prodrug for the better potency.

Although the present invention has been explained in relation to its preferred embodiment, it is to be understood that many other possible modifications and variations can be made without departing from the spirit and scope of the invention as hereinafter claimed.

What is claimed is:

1. A compound of a formula (I):

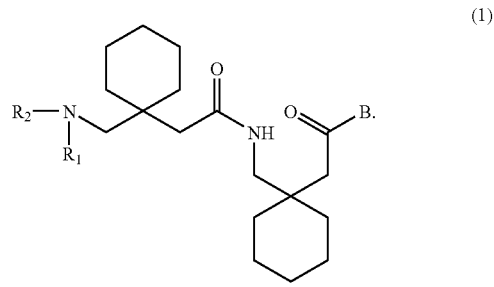

(1)

wherein
R$_1$ and R$_2$ are independently H;
B is OR$_3$, wherein R$_3$ is H or C$_{2-5}$ alkyl group.

2. The compound of claim 1 wherein R$_3$ is ethyl.

* * * * *